（12） United States Patent
Itu et al.

(10) Patent No.: US 11,826,175 B2
(45) Date of Patent: Nov. 28, 2023

(54) MACHINE-BASED RISK PREDICTION FOR PERI-PROCEDURAL MYOCARDIAL INFARCTION OR COMPLICATION FROM MEDICAL DATA

(71) Applicant: Siemens Healthcare GmbH, Erlangen (DE)

(72) Inventors: Lucian Mihai Itu, Brasov (RO); Tiziano Passerini, Plainsboro, NJ (US); Puneet Sharma, Princeton Junction, NJ (US); Ulrich Hartung, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 359 days.

(21) Appl. No.: 17/248,455

(22) Filed: Jan. 26, 2021

(65) Prior Publication Data
US 2021/0251577 A1   Aug. 19, 2021

(30) Foreign Application Priority Data
Feb. 17, 2020   (EP) .................................. 20464004

(51) Int. Cl.
*G06T 7/00* (2017.01)
*A61B 5/00* (2006.01)
(Continued)

(52) U.S. Cl.
CPC ............ *A61B 5/7275* (2013.01); *A61B 5/055* (2013.01); *A61B 5/346* (2021.01); *A61B 5/7267* (2013.01);
(Continued)

(58) Field of Classification Search
CPC ........ G16H 50/30; G16H 50/20; G16H 30/40; A61B 5/055; A61B 5/7267; A61B 5/7275;
(Continued)

(56) References Cited

U.S. PATENT DOCUMENTS

| 2005/0020903 A1* | 1/2005 | Krishnan | ............... | G16H 50/20 600/407 |
| 2005/0049497 A1* | 3/2005 | Krishnan | ............... | G16H 50/20 600/437 |

(Continued)

OTHER PUBLICATIONS

Dou, Kefei, et al. "An angiographic tool for risk prediction of side branch occlusion in coronary bifurcation intervention: the RESOLVE score system (Risk prEdiction of Side branch Occlusion in coronary bifurcation interVEntion)." JACC: Cardiovascular Interventions 8.1 Part A (2015): 39-46.

(Continued)

*Primary Examiner* — Duy M Dang (57) ABSTRACT

Machine-based risk prediction or assistance is provided for peri-procedural complication, such as peri-procedural myocardial infarction (PMI). A machine-learned model is used to predict risk of PMI and/or recommend courses of action to avoid PMI in PCI. Various combinations of types or modes of information are used in the prediction, such as both imaging and non-imaging data. The prediction may be made prior to, during, and/or after PCI using the machine-learned model to more quickly reduce the chance of PMI. The workflows for prior, during, and/or post PCI incorporate the risk prediction and/or risk-based recommendations to reduce PMI for patients.

20 Claims, 4 Drawing Sheets

(51) Int. Cl.
| | |
|---|---|
| G16H 50/30 | (2018.01) |
| G16H 50/20 | (2018.01) |
| G16H 30/40 | (2018.01) |
| A61B 5/346 | (2021.01) |
| A61B 5/055 | (2006.01) |
| A61B 6/03 | (2006.01) |
| A61B 6/00 | (2006.01) |
| G06N 3/04 | (2023.01) |
| G06N 3/08 | (2023.01) |
| A61B 5/02 | (2006.01) |
| A61B 8/12 | (2006.01) |

(52) U.S. Cl.
CPC .............. A61B 5/742 (2013.01); A61B 6/032 (2013.01); A61B 6/504 (2013.01); A61B 6/5217 (2013.01); G06N 3/04 (2013.01); G06N 3/08 (2013.01); G06T 7/0012 (2013.01); G16H 30/40 (2018.01); G16H 50/20 (2018.01); G16H 50/30 (2018.01); A61B 5/0066 (2013.01); A61B 5/02028 (2013.01); A61B 8/12 (2013.01); G06T 2207/20081 (2013.01); G06T 2207/20084 (2013.01); G06T 2207/30048 (2013.01)

(58) Field of Classification Search
CPC ... A61B 5/742; A61B 5/0066; A61B 5/02028; A61B 6/032; A61B 6/504; A61B 6/5217; A61B 8/12; A61B 5/346; A61B 5/02007; A61B 6/5211; G06N 3/04; G06N 3/08; G06T 7/0012; G06T 2207/20081; G06T 2207/20084; G06T 2207/30048; G06H 50/70
See application file for complete search history.

(56) References Cited

U.S. PATENT DOCUMENTS

| | | | | |
|---|---|---|---|---|
| 2014/0356356 A1* | 12/2014 | Thuren | ...................... | A61P 9/10 424/133.1 |
| 2015/0164453 A1* | 6/2015 | Choi | ....................... | A61B 6/503 600/407 |
| 2016/0292372 A1* | 10/2016 | Kamen | ................... | G16H 20/40 |
| 2017/0147768 A1* | 5/2017 | Ma | .......................... | G16H 10/20 |
| 2018/0310888 A1* | 11/2018 | Itu | ........................... | G16H 50/50 |
| 2018/0315182 A1* | 11/2018 | Rapaka | ................. | G06T 7/0012 |
| 2021/0213190 A1* | 7/2021 | Sawada | ................... | G16H 20/40 |

OTHER PUBLICATIONS

Gregg W. Stone; "Periprocedural myocardial infarction: The SCAI Is the Limit"; vol. 9 No. 21 (2016): 2229-2231.
Harada, Kazuhiro, et al. "Impact of high-density lipoprotein 3 cholesterol subfraction on periprocedural myocardial injury in patients who underwent elective percutaneous coronary intervention." Lipids in health and disease 17.21 (2018): pp. 1-7.
Her, Ae-Young, et al. "Impact of paclitaxel-coated balloon versus newer-generation drug-eluting stent on periprocedural myocardial infarction in stable angina patients." Coronary artery disease 29.5 (2018): 403-408.
Kang, Min Gyu, et al. "Coronary artery calcium score in predicting periprocedural myocardial infarction in patients undergoing an elective percutaneous coronary intervention." Coronary artery disease 29.7 (2018): 589-596.
Kawamoto, Hiroyoshi, et al. "Impact of strut width in periprocedural myocardial infarction: a propensity-matched comparison between bioresorbable scaffolds and the first-generation sirolimus-eluting stent." JACC: Cardiovascular Interventions 8.7 (2015): 900-909.
Lansky, Alexandra J., and Gregg W. Stone. "Periprocedural myocardial infarction: prevalence, prognosis, and prevention." Circulation: Cardiovascular Interventions 3.6 (2010): 602-610.
Layland, Jamie J., et al. "The index of microvascular resistance identifies patients with periprocedural myocardial infarction in elective percutaneous coronary intervention." Heart 98.20 (2012): 1492-1497.
Olivier, Christoph B., et al. "Definitions of peri-procedural myocardial infarction and the association with one-year mortality: Insights from CHAMPION trials." International journal of cardiology 270 (2018): 1-24.
Osugi, Naohiro, et al. "Impact of albuminuria on the incidence of periprocedural myocardial injury in patients undergoing elective coronary stent implantation." The American journal of cardiology 114.1 (2014): 42-46.
Park, Duk-Woo, et al. "Frequency, causes, predictors, and clinical significance of peri-procedural myocardial infarction following percutaneous coronary intervention." European heart journal 34.22 (2013): 1662-1669.
Porto, I., et al. "Plaque volume and occurrence and location of periprocedural myocardial necrosis after percutaneous coronary intervention: insights from delayed-enhancement magnetic resonance imaging, thrombolysis in myocardial infarction myocardial perfusion grade analysis, and intravascular ultrasound." (2010). pp. 662-669.
Stone, Gregg W., et al. "Plaque characterization to inform the prediction and prevention of periprocedural myocardial infarction during percutaneous coronary intervention: the CANARY Trial (Coronary Assessment by Near-infrared of Atherosclerotic Rupture-prone Yellow)." JACC: Cardiovascular Interventions 8.7 (2015): 927-936.
Usui, Eisuke, et al. "Efficacy of multidetector computed tomography to predict periprocedural myocardial injury after percutaneous coronary intervention for chronic total occlusion." International heart journal (2017): 16-114.
Wang, Le, et al. "High-dose statin pretreatment decreases periprocedural myocardial infarction and cardiovascular events in patients undergoing elective percutaneous coronary intervention: a meta-analysis of twenty-four randomized controlled trials." PLOS One 9.12 (2014): e113352.
Xia, Jinggang, et al. "Impact of glycemic variability on the occurrence of periprocedural myocardial infarction and major adverse cardiovascular events (MACE) after coronary intervention in patients with stable angina pectoris at 6 months follow-up." Clinica Chimica Acta 471 (2017): 196-200.
Zhang, Dong, et al. "Risk stratification of periprocedural myocardial infarction after percutaneous coronary intervention: analysis based on the SCAI definition." Catheterization and Cardiovascular Interventions 89.S1 (2017): 534-540.
Zhang, Qi, et al. "Correlates and outcomes related to periprocedural myocardial injury during percutaneous coronary intervention for chronic total occlusion: Results from a prospective, single center PCI registry." Catheterization and Cardiovascular Interventions 87.S1 (2016): 616-623.
Lapuerta, et al.; "Neural Network Assessment of Perioperative Cardiac Risk in Vascular Surgery Patients", Medical Decision Making, vol. 18, No. 1, Jan. 1, 1998,, pp. 70-75.
Zeitouni, at al.; "Periprocedural myocardial infarction and injury in elective coronary stenting", European Heart Journal, vol. 39, No. 13, Jan. 20, 2018, pp. 1100-1109.
Hsieh, at al.; "A fitting Machine learning prediction model for short-term mortality following percutaneous catheterization intervention a nationwide population-based study", Annals of Translational Medicine, vol. 7, No. 23, Dec. 1, 2019, pp. 32-732.
Extended European Search Report (EESR) dated Jul. 15, 2020 in corresponding European Patent Application No. 20464004.9.

* cited by examiner

MACHINE-BASED RISK PREDICTION FOR PERI-PROCEDURAL MYOCARDIAL INFARCTION OR COMPLICATION FROM MEDICAL DATA

CROSS REFERENCE TO RELATED APPLICATIONS

This application claims the benefit of European Application Serial No. 20464004.9 filed Feb. 17, 2020 which is incorporated herein by reference in its entirety.

BACKGROUND

The present embodiments relate to machine-based assistance in percutaneous coronary intervention (PCI). One common complication of catheterization in PCI is periprocedural myocardial infarction (PMI), with a prevalence of 5% to 30%, depending on the evaluation criteria. Patients with PMI have a higher risk of mortality than those without PMI.

PMI may be predicted from clinical symptoms, ECG abnormality, and blood biomarkers (e.g., CK-MB or troponin). The preferred biomarker for myocardial necrosis is cardiac troponin (I or T), which has high myocardial tissue specificity as well as high clinical sensitivity. The disadvantage of these approaches is that the PMI may only be diagnosed when clearly manifested in blood biomarkers or ECG. Existing approaches may not perform well as early risk assessment.

SUMMARY

Systems, methods, and computer readable media with instructions are provided for machine-based risk prediction or assistance for peri-procedural myocardial infarction. A machine-learned model is used to predict risk of PMI and/or recommend courses of action to avoid PMI in PCI. Various combinations of types or modes of information are used in the prediction, such as both imaging and non-imaging data. The prediction may be made prior to, during, and/or after PCI using the machine-learned model to more quickly reduce the chance of PMI. The workflows for prior, during, and/or post PCI incorporate the risk prediction and/or risk-based recommendations to reduce PMI for patients.

In a first aspect, a method is provided for machine-based risk prediction for peri-procedural myocardial infarction. A medical diagnostic imaging system images a patient. The imaging provides first image data representing an internal cardiac region of the patient. The first image data is from a first mode of data acquisition. Second data for the patient is acquired. The second data is for a second mode of data acquisition different than the first mode. A processor determines a risk of the peri-procedural myocardial infarction by input of first data responsive to the first image data and the second data to a machine-learned model. Information based on the risk is displayed.

In one embodiment, the imaging includes computed tomography imaging, magnetic resonance imaging, or intravascular imaging. The first data is an anatomical, heart disease, and/or cardiac function measurement, and is based, at least in part, from detection in the first image data. The second data may be blood test measurements, ECG measurements, genetic data, demographic data, clinical data, or percutaneous coronary intervention characteristics. For example, the second data is the blood test measurements. Other modes of data acquisition may be used, such as acquiring imaging data, blood test data, and third data for a third mode. For example, the third data is one of the ECG measurements, the genetic data, the demographic data, the clinical data, or the percutaneous coronary intervention characteristics.

In another embodiment, the risk is determined as a prediction for a future time, such as the risk of PMI 30 days after PCI. The risk may be determined as a likelihood of readmission, revascularization, length of hospitalization, death, and/or major adverse cardiac event (MACE).

In yet another embodiment, a recommendation for patient treatment is identified. The recommendation corresponds to the risk.

The risk may be determined using various machine-learned models. For example, the machine-learned model is a neural network.

The determination and/or display are performed at any one or multiple of different times relative to the PCI. For example, determining and displaying are performed prior to a percutaneous coronary intervention for the patient. As another example, determining the risk is performed multiple times during a percutaneous coronary intervention for the patient, such as with the acquisition of another image during the intervention. Displaying is performed where the risk from one of the times is above a threshold level. In another example, determining is performed multiple times after a percutaneous coronary intervention for the patient, such as each time additional data becomes available. A suggested course of action is displayed where the risk is above a threshold level.

In a second aspect, a method is for machine-based assistance for peri-procedural myocardial infarction. First data for a patient is accessed for percutaneous coronary intervention. A course of action is indicated by an artificial intelligence in response to input of the first data to the artificial intelligence. The course of action limits a risk of peri-procedural myocardial infarction. The course of action is displayed.

In one embodiment, accessing the first data includes accessing medical imaging of a cardiac region of the patient, calculating anatomical, heart disease, and/or cardiac function measurement from the imaging as a first part of the first data, and acquiring blood test measurements, ECG measurements, and demographic data as a second part of the first data.

In another embodiment, the artificial intelligence is a machine-learned neural network.

Various indications may be provided at various times relative to PCI. For example, a type of stent, medication, and/or device used in the percutaneous coronary intervention is indicated prior to the percutaneous coronary intervention. As another example, a correction is indicated during the percutaneous coronary intervention. In another example, a medication change or surgical intervention is indicated after the percutaneous coronary intervention.

In a third aspect, a method is provided for machine-based assistance for peri-procedural complication. First data for a patient for percutaneous coronary intervention is accessed. A machine-learned model determines a risk of the peri-procedural complication in response to input of the first data. A medical person involved in the percutaneous coronary intervention is informed of the risk.

In one embodiment, the medical person is informed of the risk and a recommended course of action where the risk is over a threshold.

In another embodiment, determining and informing occur as part of a workflow prior to, during, or after the percutaneous coronary intervention.

Any one or more of the aspects or concepts described above may be used alone or in combination. The aspects or concepts described for one embodiment may be used in other embodiments or aspects. The aspects or concepts described for a method or system may be used in others of a system, method, or non-transitory computer readable storage medium.

These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Automated risk prediction is provided for PMI or another complication of PCI. Early risk assessment or prevention of PMI may reduce the post-procedure major adverse cardiovascular event (MACE) rate, length of hospitalization, and/or associated costs. A data-driven approach automatically extracts and quantifies complication related features from routine medical exams (e.g. coronary angiography exams) and combines the features with other clinical biomarkers, resulting in a streamlined assessment of risk and prevention of complication. PMI will be used as an example of the complication herein.

A PMI risk score uses an AI model relying on multi-modal features. The AI-based companion indicates courses of action for preventing or limiting PMI. Advantageous workflows for pre-PCI, during-PCI, and post-PCI integrate the AI-based PMI assessment.

Figure 1:
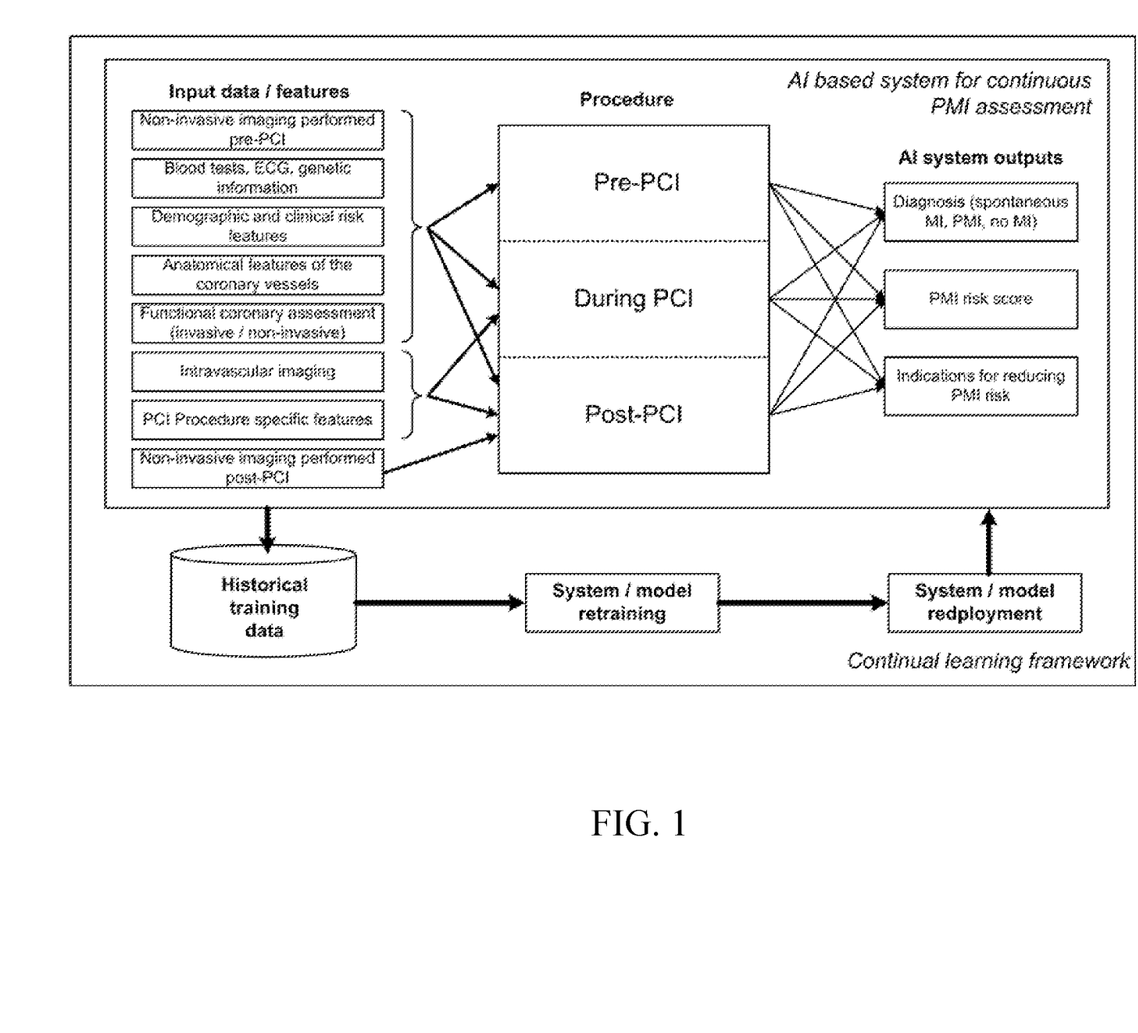
FIG. 1 illustrates use of a machine-learned model at different times relative to PCI to assist in reduction of PMI risk.

In one embodiment shown in FIG. 1, an artificial intelligence (AI)-based comprehensive system and method is provided for continuous or regular assessment of PMI. One or more, such as multiple, modes of data acquisition and corresponding data 10 are gathered for input to the machine-learned model as part of the PMI assessment 12. The PMI assessment 12 is performed at one or more of various clinical stages: pre-PCI, PCI procedure, post-PCI. The assessment 12 is performed continuously, periodically, or as data is acquired. The assessment 12 outputs 13 a risk level, such as outputting a diagnosis for a given patient as one of spontaneous MI, periprocedural MI, or no MI. The distinction between spontaneous MI (acute CAD) and periprocedural MI may be based on various considerations, such as any given CK-MB or troponin level. The absolute risk from spontaneous MI may higher than from periprocedural MI. The output 13 may be a PMI risk score at any given time point (pre-PCI, post-PCI, during PCI), indicating the risk of the patient to a suffer a PMI. One or more indications for reducing the risk of PMI (e.g., preferred or suggested course of action) may be output 13 at any given time point relative to PCI.

In approximately 20% of PMI cases, no mechanical causes for PMI can be found. Micro-embolization of thrombotic or atherosclerotic material may be the cause but may be undetectable in coronary angiograms. The AI-based system, accounting for multiple modes of data acquisition, may more likely be able to detect at least a subset of the 20% of PMI cases in which no explicit mechanical causes for PMI can be identified. Measures for prevention may be provided where such measures may not otherwise be triggered. The PMI assessment and prevention by the AI-based system may reduce the post-procedure MACE rate, length of hospitalization, associated costs, and/or failure to identify PMI risk. The disadvantage of existing approaches is that the PMI can only be diagnosed when clearly manifested in blood biomarkers or ECG. The AI-based system may perform an early risk assessment or indicate measures for prevention in other circumstances.

To assist in PMI prevention in PCI patients, the AI automatically detects imaging and/or non-imaging characteristics and features associated with PMI, provides a risk score for fine grained assessment of PMI risk, provides indications during the PCI procedure (e.g., in case of high risk of PMI), and/or self improves in time with the accumulation of data. Improved CAD patient care and outcome may be provided, such as during cathlab interventions. An elevated or high risk of PMI may be detected automatically. Due to the detection of increased risk, countermeasures may be proposed, and a PMI may be avoided.

For training, historical training data 14 is used. The training data 14 includes many samples (e.g., hundreds or thousands) of input data sets (e.g., images, information derived from images, other measurements (e.g., lab, blood, and/or genetic), patient information (e.g., demographic or clinical), and/or other data from different modes of acquisition. The modes of acquisition represent different types of information and/or measurements, such as different types of imaging (angiography, computed tomography, magnetic resonance, ultrasound, and/or optical modes). The training data also includes ground truths, such as diagnosis (e.g., spontaneous MI, PMI, no MI), PMI risks and courses of action established by experts for each dataset. For a multi-task machine-learned model, the ground truth may include ground truth segmentation or feature locations. The ground truths may be annotations from experts or data mined from patient records. In one embodiment, troponin levels are used as the ground truth for risk or likelihood of PMI.

Figure 3:
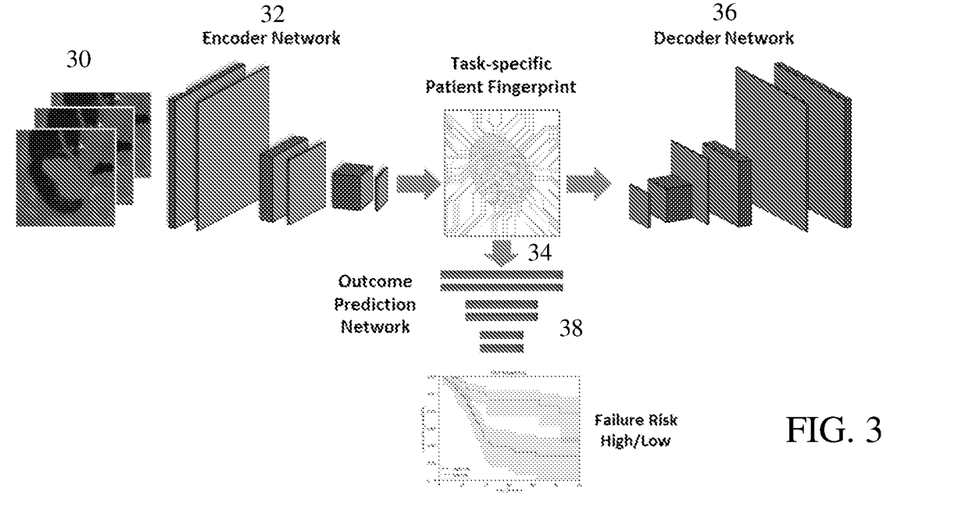
FIG. 3 shows an example machine-learned architecture for risk prediction.

The architecture of the model to be trained is defined. In one embodiment, the architecture is defined as a multi-task architecture. The network architecture includes an output layer for each task, such as one output layer for segmentation or estimation of image features (e.g., lesions and/or other anatomical features associated with PMI) and another output layer or layers for risk, diagnosis, and/or recommended courses of action. FIG. 3 shows an example embodiment with the network architecture including an encoder 32, bottleneck 34, and decoder 36 (e.g., together forming an autoencoder of a U-Net or image-to-image neural network) used to train for segmentation or image feature estimation. For application, the decoder 36 may not be used. For risk, diagnosis, and/or course of action prediction, the network architecture includes a convolutional neural network 38 connected to receive output of the encoder 32 or the bottleneck 34 as input. The convolutional neural network 38 outputs the classification of risk. The encoder 32 receives the input data 30, which is encoded by the encoder 32. The resulting abstractions or features output by the encoder 32 at the bottleneck 34 are a fingerprint to be learned based on optimization using ground truths for the output of the decoder 36 as one task and the output or outputs of the outcome prediction network 38 for another task or tasks.

Other network architectures may be used. In other embodiments, generative, image-to-image, or generative adversarial network (GAN) network architectures are used, such as a U-net type of arrangement with down sampling and up sampling blocks or layers with or without skip connections. For multi-task in a GAN, the GAN includes two or more discriminator networks or layer arrangements. A discriminator network is provided for each task. In other approaches, a network to learn a policy for action decisions in reinforcement learning is used. A convolutional neural network, recurrent neural network, or fully connected neural network may be used. Where the machine-learned model is to be applied continuously or at different time points relative to PCI, a recurrent neural network, which uses long-term short-term memory or other temporal arrangements, may use information from different times for a current output.

For machine training the model, the machine learning architecture arrangement is defined. The definition is by configuration or programming of the learning. The number of layers or units, type of learning, order of layers, connections, and other characteristics of the network are controlled by the programmer or user. In other embodiments, one or more aspects of the architecture (e.g., number of nodes, number of layers or units, or connections) are defined and selected by the machine during the learning.

A machine implements the training of the defined architecture using the training data. The input features may be manually defined. Some or all of the features may be learned from raw data input, such as for deep learning. The machine (e.g., processor, computer, workstation, or server) machine trains the defined network (e.g., the defined multi-task generator). The network is trained to generate outputs for one or more tasks, such as multiple tasks.

For training any of the networks, various optimizers may be used, such as Adadelta, SGD, RMSprop, or Adam. The weights, connections, filter kernels, and/or other learnable variables of the network are randomly initialized, but another initialization may be used. End-to-end training is performed, but one or more features may be set. The network for one task may be initially trained alone, and then used for further training of that network for the one task and a further network for the other task. Separate losses may be provided for each task. Joint training may be used. Any multi-task training may be performed. Batch normalization, dropout, and/or data augmentation are not used, but may be (e.g., using batch normalization and dropout). During the optimization, the different distinguishing features are learned. The features providing an indication of outcome and/or indication of another task are learned.

The optimizer minimizes an error or loss, such as the Mean Squared Error (MSE), Huber loss, L1 loss, or L2 loss. The same or different loss may be used for each task. In one embodiment, the machine training uses a combination of losses from the different tasks.

The trained model is stored. The network parameters, such as connections, convolution kernels, weights, or other learned values for the network are stored. The network is stored in memory to be used for application or testing. Once trained, the machine-learned model may be applied to estimate an outcome (e.g., diagnosis, risk for PMI, and/or indication or recommendation of action to take). The many samples in the training data are used to learn to output given an unseen sample of input data for a future or given patient.

FIG. 1 shows the AI-based system for continuous or updated assessment of PMI embedded in a continual learning framework. Although initially based on an existing large database with patient-specific records, the system may be updated, such as to continuously learn, or retrained 15 from new data. The retrained machine-learned model 16 is redeployed for use with other patients. As further examples or samples for different patients are provided, such as due to application of the machine-learned model and observation of complications from PCI, these further examples are used to update the training and corresponding machine-learned model.

Figure 2:
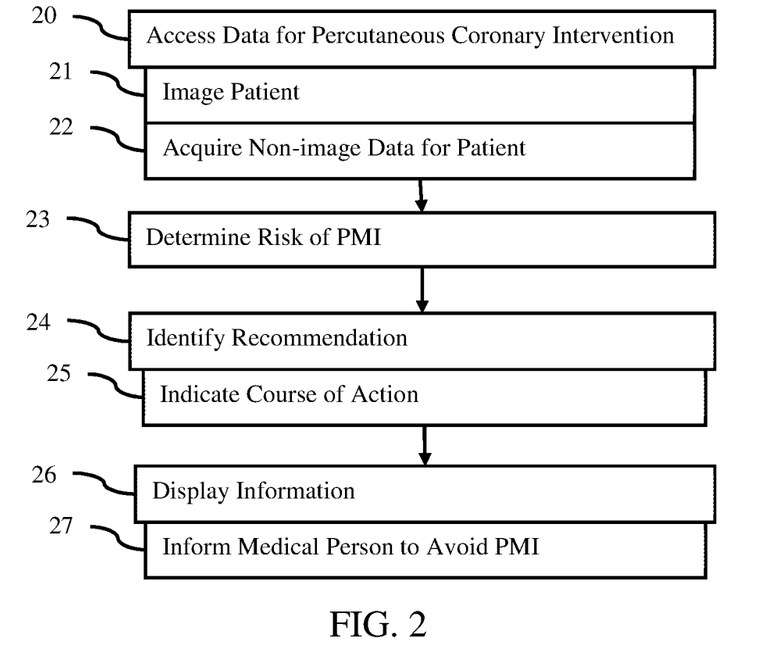
FIG. 2 is a flow chart diagram of one embodiment of a method for machine-based risk prediction for peri-procedural complication.

FIG. 2 is a flow chart diagram of one embodiment of a method for machine-based risk prediction for complication, such as PMI. Assistance for PMI, such as providing diagnosis, risk, and/or course of action, is provided using AI. Multiple, such as five or more, modes of data acquisition are provided for more informed or comprehensive AI assistance. The workflows for PCI are altered to include the assistance, especially as AI may operate quickly on time frames matched to PCI where a person may not provide such rapid analysis of the volume of information.

The method is performed in the order shown (e.g., top to bottom or numerical), but other orders may be used. For example, acts 21 and 22 are performed in any order. As another example, act 24 is performed before act 23.

Additional, different or fewer acts may be provided. For example, acts 21, 22, 23, 24, 25, 26, and/or 27 are not performed. One of acts 23 or 24/25 may be provided without the other. Acts 26/27 may not be provided, such as where the estimated risk is low.

The method is performed by a medical diagnostic scanner, a workstation, a server, or a computer. Remote, such as cloud based, or local application of the AI may be used. For example, a scanner and/or memory are used to acquire or access data for a patient. A processor, such as an image processor of the scanner or a separate computer, predicts the risk, diagnosis, and/or course of action. The image processor uses a display screen or printer for display or informing. A physician may use the output information to assist in making a treatment decision for the patient. The information may result in better treatment and/or diagnosis for the patient.

In act 20, data for a patient is accessed. A processor accesses memory. Using mining, search, or look-up, stored data in a medical records database, computerized patient or health record, lab database, and/or other memory is accessed. Access may be provided by receiving a transmission, such as in response to a query or push. Access may be provided by manual input of information. Access may be provided by scanning, sensing, or measuring from a patient. Different data, such as from different modes of acquisition, may be accessed from the same or different ways, locations, or devices.

The data is for PCI or associated complication. Any data relevant for PCI, such as data gathered prior to, during, and/or after PCI, is accessed. Any data indicative of risk of PMI is accessed.

The data may be imaging data of act 21 and/or non-image data of act 22. For act 21, one or more medical diagnostic imaging systems image a patient. The imaging provides image data representing an internal cardiac region of the patient, such as a point, line, area, or volume of the patient.

Computed tomography imaging, magnetic resonance imaging, x-ray angiography, fluoroscopy, optical, ultrasound, optical coherence tomography, and/or intravascular imaging and corresponding scanners may be used. Each type of scanning provides one or more modes of data acquisition. Any number of modes may be provided.

The image data itself may be accessed for input to the machine-learned model. Data derived from image processing may be accessed (e.g., created or calculated) for input to the machine-learned model. The image data is used to determine anatomical, heart disease, and/or cardiac function measurements. These measurements are detected, at least in part, from the image data. Any of these features may be extracted automatically (e.g., performing image processing on the available invasively or non-invasively acquired images).

In one embodiment, non-invasive imaging performed pre-PCI is used. High coronary artery calcium score (CACS), measured with CCTA, may be determined for input. Lesion length and/or the presence of the napkin-ring sign may be detected from CCTA. Plaque composition, such as lipid-rich lesions, as assessed with CCTA, may be detected.

Other non-invasive imaging performed pre- or post-PCI may be used. For example, PMI following PCI can be visualized and quantified using cardiac magnetic resonance imaging (MRI). Cardiac MRI is used to determine ventricular infarct size. Contrast-enhanced (CE)-MRI may be used for quantification of <1 g of infarcted myocardium.

Intravascular or non-invasive imaging (e.g., x-ray angiography) acquired during the PCI procedure may be used. For example, intravascular ultrasound (IVUS) or optical coherence tomography (OCT) and/or metrics extracted from the intravascular images (e.g., lumen and/or plaque related features) may be used.

Anatomical features assessed pre-PCI (from non-invasive images) and during the PCI procedure may include vessel tortuosity, number of lesions, lesions in specific vessels (LAD, LM), bifurcation lesions and/or Medina classification, bifurcation angle (e.g., a wide bifurcation angle is associated with a higher risk of side branch occlusion, and, thus, with a higher risk of PMI), diameter ratio between main branch and side branch, long lesions, overall disease burden, and/or thrombus. Functional assessment (e.g., fractional flow reserve, higher pre-PCI index of microvascular resistance (IMR), or other flow or pressure measurements) may include invasive measurements and/or measurements determined from non-invasive imaging.

In act 22, non-image data is accessed. Data from other modes of acquisition for the patient is acquired. The data is extracted automatically and/or manually. The non-image data is from sensors, the computerized patient medical record, manual input, pathology database, laboratory database, and/or other source. The non-image data represents one or more characteristics of the patient, such as family history, medications taken, temperature, body-mass index, and/or other information. For example, genomic (genetic), ECG, blood test (e.g., troponin level), demographic, clinical, measurement, molecular, and/or family history data of the patient are acquired from memory, transform, data mining, and/or manual input. In another example, characteristics of the PCI procedure for the patient are acquired, such as a course of PCI including a sequence of therapy events, the devices used, and/or the region of application for each event. The data for one or more of these different acquisition modes are acquired, such as acquiring two, more, or all of blood tests, ECG measurements, genetic data, demographic data, clinical data, or the PCI characteristics for a patient.

Example PCI procedure-specific features include total procedure time (may also be predicted during the pre-PCI stage using an AI model), number and type of stents, number of vessels treated, stent overexpansion, side branch occlusion, dissection, (distal) embolization, spasm, no reflow or small reflow (as assessed through the TIMI flow grade), and/or disruption of collateral flow. Example blood test measurements include CK-MB and (hS)Troponin, blood glucose variability, high-density lipoprotein cholesterol (HDL-C), and/or HDL-C subfractions, such as HDL2 cholesterol (HDL2-C) or HDL3 cholesterol (HDL3-C). Since PMI alters the ECG waveform, ECG measurements, such as for spontaneous MI (acute CAD), may be used. Genetic information is obtained through sequencing as a direct or indirect indicator. Demographic and clinical risk features include age, gender, hypertension, and/or renal dysfunction. Diagnosis of albumonuria (pathological condition wherein the protein albumin is abnormally present in the urine) may be used as non-image data. The type of catheter intervention (e.g., CTO vs. non-CTO treatment) may be accessed. Generic cardiovascular disease related risk score (e.g. Framingham) or PMI specific risk score (e.g. risk score for side branch occlusion) may be calculated. Data may be extracted from a radiology report, such as by using natural language processing (NLP). Measurements from non-invasive stress tests may be used. The patient condition, such as stable, ACS (STEMI/NSTEMI, UA), or CTO may be used. The clinical and/or medication history of the patient may be used. Other comorbidities in addition to the disease that is being treated may be used.

In act 23, a processor determines a risk of the PMI and/or diagnosis. The accessed data (e.g., data from different modes of acquisition such as image and non-image data) for the patient is input to the machine-learned model. In response to the input, the machine-learned model outputs the outcome (e.g., diagnosis and/or risk of PMI). The prediction or estimate of outcome uses AI. The machine-learned model, such as a machine-learned neural network, predicts based on the input. The scan data and/or non-image data are input for the prediction, which is performed by AI.

Any machine-learned model resulting from the machine training may be used. For example, a support vector machine, clustering, or other generator is provided for generating an estimate of the outcome based on the input. A machine-learned classifier may be used. In one embodiment, a neural network is trained as the generator, such as a trained convolutional neural network (CNN). Reinforcement model, recurrent neural network model, convolutional neural network, fully connected neural network, U-Net, densenet, or another model may be used. Any forward model may be used, such as the multi-task network of FIG. 3. For a reinforcement learning-based approach, the machine-learned or AI agent proposes an action at any given time point. Example actions include do nothing or implant a SES stent based on the level of risk as incorporated into the learned policy. For a machine-learned recurrent neural network, the data or features are acquired for different times (e.g., discrete or continuous). The recurrent neural network analyzes and predicts based on the evolution in time of processes.

The output may be the risk of PMI for the patient, the diagnosis (no PMI, PMI, or spontaneous MI), and/or level of PMI. PMI may range from a minor elevation of cardiac enzymes to a large-sized infarct. Thus, the AI may estimate the type of PMI that may occur and the likelihood (e.g. by assessing the size and/or volume of the myocardium subtended by the side branch at risk of occlusion and other input data).

The risk is a likelihood of PMI occurring. The risk may be predicted for any time, such as the current time or a future time. For example, the risk output may refer to risk at one or more of various time points: 1 day, 3 days, 30 days, 6 months, 12 months, 3 years, 5 years, and/or 10 years.

The risk is of PMI occurrence. Other PMI risks may be risk of readmission, revascularization, length of hospitalization, major adverse cardiac event (MACE), death, or other events due to, at least in part, PMI.

In act 24, the processor identifies a recommendation for patient treatment. The recommendation is generated as an output for the machine-learned model. Alternatively, the diagnosis and/or risk output by the machine-learned model, with or without other information for the patient, is used to generate a recommendation. A coded program is use used to recommend, such as using guidelines given the level of risk of PMI.

Various types of indications (e.g., recommendations) may be provided by the AI-based system. The type of stent to be implanted (e.g., bioresorbable scaffolds (BRS) versus first-generation sirolimus-eluting stents (SES)) may be recommended. BRS have been associated with a higher incidence of PMI, mainly due to a higher abluminal strut surface area. If the risk of PMI is below a threshold, then the BRS is recommended to prevent acute recoil or occlusion, allowing sealing of post-procedural dissections following acute barotrauma, and providing inhibition of in-segment restenosis through efficient drug-elution. In the case of high risk of PMI, BRS may represent a suboptimal solution so SES is recommended. In patients with stable angina, using a PCB (Paclitaxel-Coated Balloon) compared with deployment of a DES (Drug-Eluting Stent) is associated with a significant reduction in the risk of PMI. Where the risk of PMI is above a threshold, then PCB is recommended. For higher risk of PMI, then a high-dose statin pretreatment may be recommended. Antithrombotic and antiplatelet (e.g. clopidogrel, prasugrel) agents may be recommended based on the level of PMI risk. The use of devices which protect against distal embolization may be recommended for higher risk of PMI.

In act 25, the processor indicates a course or courses of action. The AI, in response to input of the data, outputs one or more courses of action. Alternatively, the diagnosis and/or risk of PMI are output and used to select the course or courses of action, such as from a look-up table. The course of action is selected to limit the risk of PMI for the patient.

The recommendation of a course of act is indicated in act 25, such as through the display of act 26 or informing of act 27. The type of stent, medication, and/or device used in the PCI is indicated prior to the PCI. A correction (e.g., repositioning of a stent, replacement of a stent, ablation, removal of occlusion, dissection, embolization, fixing a spasm, altering reflow, or altering cardiac flow) or medication is indicated during PCI. A medication change or surgical intervention is indicated after the PCI.

In act 26, a display screen or report (e.g., printed page) displays information based on the risk. The information is the diagnosis, risk, and/or course of action. The display is a visual output. The image processor generates an image. The image may be output to a display, into a patient medical record, and/or to a report.

The risk, diagnosis, and/or action may be an annotation, alphanumeric text, graph, or chart. For example, the risk of PMI is displayed as a graph of probability as a function of time. As another example, stratification results are displayed. The output is projected to the display for the physicians.

The input data, such as the data most important or reflective of the risk as estimated by the machine-learned model, may be output. For example, an image showing anatomy indicative of higher risk is output with an annotation of the value of the risk of PMI. Other information may be displayed with the predicted risk. More than one prediction may be output, such as outcome predictions for different therapies and/or times. Risks resulting from taking different courses of action may be output, such as in a table.

The diagnosis, risk, and/or action may be presented with or on (e.g., overlay or annotation) an image of the patient. For example, an image of a slice through a cardiac region is displayed. The outcome is provided with the image of the anatomical structure of interest, such as the heart, vessel, or valve, on a display screen. Where 3D scan data is provided, the 3D scan data is rendered to a 2D plane. Any rendering may be used, such as projection rendering. The display may include information from one or more similar patients.

In act 27, the processor informs a medical person involved in the PCI of the risk. The person is informed visually and/or audibly. For example, a warning of PMI risk is displayed on a display screen as part of act 26 and/or through audio output by a speaker. The determined risk of PMI, diagnosis, and/or course of action from the machine-learned model in response to input of the multi-modal patient data is output to the medical professional, such as a doctor or nurse involved in the PCI or patient treatment.

The information, such as a recommended course of action with or without the risk, is provided in response to the risk being over a threshold level. Multiple thresholds may be provided where each range of PMI risk maps to different courses of recommended actions. Where the risk may be mitigated, a threshold is provided to inform those responsible for the PCI or patient care of the mitigation. Alternatively, the recommended course of action, which may be to make no changes, is provided based on the risk even for low risk of PMI. The information is provided for any level of PMI risk to assist in treatment. In yet other alternatives, the machine-learned model outputs the recommended course of action without thresholding, which course of action is output to the medical professional to inform them of the recommendation.

The determination of act 23 and informing of act 27 occur as part of a PCI workflow prior to, during, and/or after the PCI. For example, the application of the machine-learned model and display of the output results are performed as part of a pre-PCI assessment, such as an assessment for PMI. The workflow includes four steps. First, a patient with suspected coronary artery disease (CAD), e.g. chest pain, is examined. Demographic, clinical, genetic, and/or other risk features are evaluated by a physician. Second, a CCTA imaging examination is performed and blood tests are run. Third, if the patient is diagnosed with CAD, the above described AI-based system is employed to evaluate the risk of PMI. The AI-based system may be employed once or repetitively as additional data is gathered. Fourth, the patient is scheduled for invasive coronary angiography, and the interventional cardiology team is informed before the procedure of the PMI risk, PMI diagnosis, and/or recommended course of action. In one embodiment, the risk notification is performed only if PMI risk is enhanced (above a threshold or enhanced as diagnosed).

In another example, the risk determination is performed multiple times during PCI, such as each time an image scan is performed. Anytime the risk is above a threshold or in response to each risk determination, the risk, diagnosis, and/or recommendation are displayed to a medical professional. During-PCI, PMI assessment is performed. First, the patient with acute CAD is scheduled for an emergency invasive coronary angiography examination. Optionally, past medical images of the patient (e.g. past CCTA exams) are input into the AI-based PMI assessment system. The PMI risk, diagnosis, and/or recommendation are provided at the beginning of the PCI. Second, invasive coronary angiography is performed, and the culprit lesion is stented. PMI risk is automatically assessed continuously, periodically, and/or multiple times during the intervention. The PMI risk is assessed by the AI-based system in response to new data. Higher risk may reflect stent overexpansion, side branch occlusion, dissection, (distal) embolization, spasm, no or small reflow, or disruption of collateral flow. If the risk of PMI exceeds a certain threshold (a priori or dynamically defined), the interventional cardiology team is informed during the procedure. Due to the AI-based speed of risk determination, the cardiology team has the chance to intervene to reduce the risk. The possible cause or causes of the PMI risk may be mitigated.

As another example, the risk determination is performed one or more (e.g., multiple) times after the PCI for the patient. Any time the risk is above a threshold or in response to each risk determination, the risk, diagnosis, and/or recommendations are displayed to a medical professional. For post-PCI, PMI assessment is performed. After the invasive coronary angiography procedure is performed for a patient with acute or stable CAD, the patient is monitored post-PCI continuously for PMI risk using the AI-based assessment system. The PMI risk is determined as new data becomes available or periodically, such as when new blood test results are available and/or in response to image scans. In one embodiment, the patient wears a wearable sensor, such as a pressure, heart rate, or ECG sensors. The PMI risk is determined regularly as new sensor data is acquired. Following repeated blood tests, CK-MB and (hS)Troponin may be found to be elevated. Other problems indicating PMI risk may be present. The AI-based system determines a PMI risk exceeding a threshold, so a suggested course of action, e.g. modify medication, bring patient immediately to the cathlab, increase monitoring, and/or other action, is presented to the medical professional.

In other embodiments, the machine-learned model is trained and used to assess other peri-procedural complications. Thrombosis, stroke, major bleeding, or death may be assessed. Combinations of multiple different complications may be assessed by different machine-learned models, one for each complication, and/or by one machine-learned model trained to output risk, diagnosis, and/or course of action for multiple complications.

The physician treats the patient based, in part, on the machine-learned model output. The physician uses information about the patient and the output risk, diagnosis, and/or recommendation to select a therapy or to not select a therapy. The output is used by the physician to assist in treatment decisions.

Figure 4:
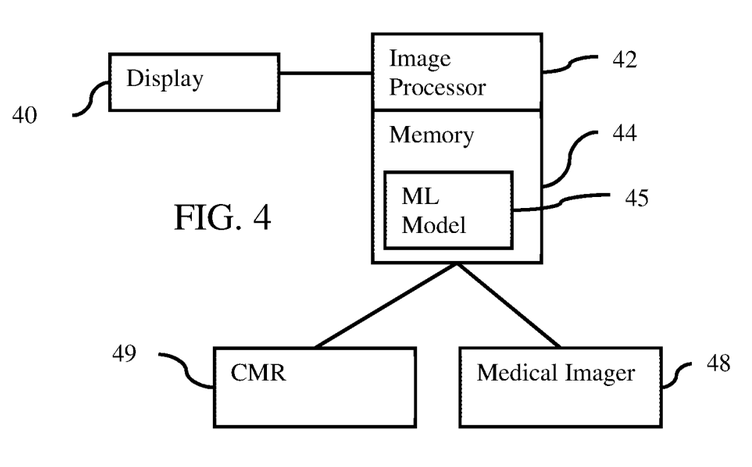
FIG. 4 is a block diagram of one embodiment of a system for PMI risk prediction or PMI avoidance assistance.

FIG. 4 shows a medical system for PMI or per-procedural complication risk assessment. The system generates a predication of risk, diagnosis, and/or recommended course of action, such as before, during, or after PCI.

The medical system includes the display 40, memory 44, and image processor 42. The display 40, image processor 42, and memory 44 may be part of the medical imager 48, a computer, server, workstation, or other system for image processing medical images from a scan of a patient. A workstation or computer without the medical imager 48 and/or computerized medical record database 49 may be used as the medical system.

Additional, different, or fewer components may be provided. For example, a computer network is included for remote estimation based on locally captured scan and/or other data. As another example, a user input device (e.g., keyboard, buttons, sliders, dials, trackball, mouse, or other device) is provided for user input of data used to estimate risk.

The medical imager 48 is a computed tomography, magnetic resonance, ultrasound, positron emission tomography, optical coherence tomography, intracardiac imaging, or single photon emission computed tomography scanner. For example, the medical imager 48 is a computed tomography system having an x-ray source and detector connected to a moveable gantry on opposite sides of a patient bed.

The medical imager 48 is configured by settings to scan a patient. The medical imager 48 is setup to perform a scan for the given clinical problem, such as a cardiac scan. The scan results in scan or image data that may be processed to generate an image of the interior of the patient on the display 40. The scan or image data may represent a three-dimensional distribution of locations (e.g., voxels) in a volume of the patient and may be used to detect anatomy and/or derive information indicative of PMI risk.

The image processor 42 is a control processor, general processor, digital signal processor, three-dimensional data processor, graphics processing unit, application specific integrated circuit, field programmable gate array, artificial intelligence processor or accelerator, digital circuit, analog circuit, combinations thereof, or other now known or later developed device for processing medical image data. The image processor 42 is a single device, a plurality of devices, or a network. For more than one device, parallel or sequential division of processing may be used. Different devices making up the image processor 42 may perform different functions. In one embodiment, the image processor 42 is a control processor or other processor of a medical diagnostic imaging system, such as the medical imager 48. The image processor 42 operates pursuant to stored instructions, hardware, and/or firmware to perform various acts described herein.

In one embodiment, the image processor 42 is configured to train one or more machine learning networks. Based on a user provided or other source of the network architecture and training data (e.g., from the database 49 and/or the imager 48), the image processor 42 learns features for encoders, decoders, or other network parts to train the network.

Alternatively or additionally, the image processor 42 is configured to apply one or more machine-learned models 45. For example, the image processor 42 applies scan data from the imager 48 and data from the database 49 for a patient to the machine-learned model 45. The network estimates a PMI risk, diagnosis, and/or treatment.

The image processor 42, using the machine-learned model 45, estimates a risk in response to input of data from different acquisition modes. The input data is accessed from the imager 48, the database 49, and/or another source (e.g., user input or network interface).

The image processor 42 is configured to generate an image. An image showing the risk, diagnosis, and/or recommendation for PMI is generated. The outcome may be displayed with an image of the interior of the patient, such as a computed tomography image.

The display 40 is a CRT, LCD, projector, plasma, printer, tablet, smart phone, or other now known or later developed display device for displaying the output, such as an image with the risk and recommendation.

The training data, network definition, features, machine-learned model 45, image data, non-image data, detected anatomy, risk, diagnosis, recommended course of action and/or other information are stored in a non-transitory computer readable memory, such as the memory 44. The memory 44 is an external storage device, RAM, ROM, database, and/or a local memory (e.g., solid state drive or hard drive). The same or different non-transitory computer readable media may be used for the instructions and other data. The memory 44 may be implemented using a database management system (DBMS) and residing on a memory, such as a hard disk, RAM, or removable media. Alternatively, the memory 44 is internal to the processor 42 (e.g. cache).

The instructions for implementing, by execution by the processor 42, the training or application processes, the methods, and/or the techniques discussed herein are provided on non-transitory computer-readable storage media or memories, such as a cache, buffer, RAM, removable media, hard drive or other computer readable storage media (e.g., the memory 44). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for machine-based risk prediction for peri-procedural myocardial infarction associated with a particular percutaneous coronary intervention, the method comprising:

imaging, by a medical diagnostic imaging system, a patient, the imaging providing first image data representing an internal cardiac region of the patient, the first image data being from a first mode of data acquisition;

acquiring second data for the patient, the second data being for a second mode of data acquisition different than the first mode;

determining, by a processor, a risk of the peri-procedural myocardial infarction associated with the particular percutaneous coronary intervention by input of first data responsive to the first image data and the second data to a machine-learned model;

determining, by the processor and based on the risk, a predicted outcome from among at least: no myocardial infarction, spontaneous myocardial infarction, and the peri-procedural myocardial infarction associated with the particular percutaneous coronary intervention; and displaying an indicator for the predicted outcome.

2. The method of claim 1 wherein imaging comprises computed tomography imaging, magnetic resonance imaging, x-ray angiography, or intravascular imaging, and wherein the first data comprises anatomical, heart disease, and/or cardiac function measurement, the first data based, at least in part, from detection in the first image data.

3. The method of claim 1 wherein acquiring the second data comprises acquiring blood test measurements, ECG measurements, genetic data, demographic data, clinical data, or percutaneous coronary intervention characteristics.

4. The method of claim 3 wherein acquiring the second data comprises acquiring the blood test measurements; and the method further comprising acquiring third data for a third mode, the third data comprising one of the ECG measurements, the genetic data, the demographic data, the clinical data, or the percutaneous coronary intervention characteristics.

5. The method of claim 1 wherein determining the risk comprises determining the risk as a prediction for a future time.

6. The method of claim 1 wherein determining the risk comprises determining a likelihood of readmission, revascularization, length of hospitalization, death, and/or major adverse cardiac event (MACE).

7. The method of claim 1 further comprising identifying a recommendation for patient treatment, the recommendation corresponding to the risk.

8. The method of claim 1 wherein determining comprises determining with the machine-learned model comprising a neural network.

9. The method of claim 1 wherein determining and displaying are performed prior to performance of the particular percutaneous coronary intervention for the patient.

10. The method of claim 1 wherein determining is performed multiple times during performance of the particular percutaneous coronary intervention for the patient, and wherein the further includes displaying information at a time that the determined risk from one of the times is above a threshold level.

11. The method of claim 1 wherein determining is performed multiple times after the particular percutaneous coronary intervention is performed on the patient, and wherein the method further includes displaying the information as a suggested course of action where the risk is above a threshold level.

12. A method for machine-based assistance for peri-procedural myocardial infarction, the method comprising:

accessing first data for a patient for percutaneous coronary intervention;

determining, by an artificial intelligence in response to input of the first data to the artificial intelligence, a predicted outcome from among at least: no myocardial infarction, spontaneous myocardial infarction, and a peri-procedural myocardial infarction associated with a particular percutaneous coronary intervention;

indicating a course of action by the artificial intelligence, the course of action limiting a risk of the peri-procedural myocardial infarction associated with the particular percutaneous coronary intervention; and displaying the course of action.

13. The method of claim 12 wherein accessing the first data comprises medical imaging a cardiac region of the patient, calculating anatomical, heart disease, and/or cardiac function measurement from the imaging as a first part of the first data, and acquiring blood test measurements, ECG measurements, and demographic data as a second part of the first data.

14. The method of claim 12 wherein indicating comprises indicating by the artificial intelligence comprising a machine-learned neural network.

15. The method of claim 12 wherein indicating comprises indicating a type of stent, medication, and/or device used in the percutaneous coronary intervention prior to the percutaneous coronary intervention.

16. The method of claim 12 wherein indicating comprises indicating a correction during the percutaneous coronary intervention.

17. The method of claim 12 wherein indicating comprises indicating a medication change or surgical intervention after the percutaneous coronary intervention.

18. A method for machine-based assistance for peri-procedural complication, the method comprising:

accessing first data for a patient for percutaneous coronary intervention;

determining a risk of the peri-procedural complication by a machine-learned model in response to input of the first data;

determining, consistent with the risk, a predicted outcome from among at least: no myocardial infarction, spontaneous myocardial infarction, and a Peri-procedural myocardial infarction associated with a particular percutaneous coronary intervention; and informing a medical person involved in the percutaneous coronary intervention of the predicted outcome.

19. The method of claim 18 wherein informing comprises informing of the risk and a recommended course of action where the risk is over a threshold.

20. The method of claim 18 wherein determining and informing occur as part of a workflow prior to, during, or after the percutaneous coronary intervention.

* * * * *